US008269197B2

(12) United States Patent
Goer et al.

(10) Patent No.: US 8,269,197 B2
(45) Date of Patent: Sep. 18, 2012

(54) METHOD AND SYSTEM FOR ELECTRON BEAM APPLICATIONS

(75) Inventors: Donald A. Goer, Sunnyvale, CA (US); Alexandre S. Krechetov, Mountain View, CA (US)

(73) Assignee: Intraop Medical Corporation, Sunnyvale, CA (US)

( * ) Notice: Subject to any disclaimer, the term of this patent is extended or adjusted under 35 U.S.C. 154(b) by 571 days.

(21) Appl. No.: 12/460,723

(22) Filed: Jul. 22, 2009

(65) Prior Publication Data

US 2011/0017920 A1 Jan. 27, 2011

(51) Int. Cl.
*G21K 5/04* (2006.01)
*A61N 5/00* (2006.01)

(52) U.S. Cl. .............. 250/492.3; 250/491.1; 250/492.1; 600/1; 600/2

(58) Field of Classification Search ............... 250/491.1, 250/492.1, 492.3; 600/1, 2
See application file for complete search history.

(56) References Cited

U.S. PATENT DOCUMENTS

| | | | |
|---|---|---|---|
| 4,987,309 | A | 1/1991 | Klasen et al. |
| 5,321,271 | A | 6/1994 | Schonberg et al. |
| 5,418,372 | A | 5/1995 | Schonberg et al. |
| 5,661,377 | A | 8/1997 | Mishin et al. |
| 6,422,748 | B1 | 7/2002 | Shepherd et al. |
| 2004/0079899 | A1* | 4/2004 | Ma ............................. 250/492.3 |
| 2005/0259786 | A1* | 11/2005 | Fantini et al. .................. 378/65 |
| 2006/0033044 | A1 | 2/2006 | Gentry et al. |
| 2008/0078957 | A1* | 4/2008 | Graf et al. ................. 250/492.21 |

FOREIGN PATENT DOCUMENTS

| | | |
|---|---|---|
| JP | 07051395 A | 2/1995 |
| WO | WO 91/13633 | 9/1991 |
| WO | WO 00/43045 | 7/2000 |
| WO | WO 00/66182 | 11/2000 |
| WO | WO 02/20500 | 3/2002 |
| WO | WO 2007/041546 | 4/2007 |
| WO | WO 2008/154927 | 12/2008 |

OTHER PUBLICATIONS

Applicator and Bolus Selection, Intraop PowerPoint presentation describing use of the Mobetron (2004), 1 page.
Janssen et al., "Prototyping a large field size IORT applicator for a mobile linear accelerator", Physics in Medicine and Biology, 53 (2008), pp. 2089-2102.
Leibel et al., "Electron Beam Therapy in Clinical Practice", Textbook of Radiation Oncology, 1$^{st}$ edition (1998), chapter 2, p. 219.

(Continued)

*Primary Examiner* — David A Vanore
*Assistant Examiner* — Nicole Ippolito
(74) *Attorney, Agent, or Firm* — Ropes & Gray LLP

(57) ABSTRACT

The present invention relates to methods and systems for use of an electron beam system. The electron beam system may be used within a treatment center with very little radiation shielding. The electron beam system may be used in conjunction with low-z moderators that reduce the energy level of the electron beam without the need for complex or expensive energy control systems. The electron beam system may be used to treat skin cancer and dermatological patients in non-traditional treatment facilities, as well as invasive cancers, either in an unshielded operating room to deliver intraoperative radiation therapy ("IORT") or in an unshielded room in the oncology department to deliver electron beam radiation treatment ("EB-RT").

32 Claims, 5 Drawing Sheets

OTHER PUBLICATIONS

Mobetron Operators Manual, Document No. 20440-1 Rev D (Sep. 2005), pp. 36-38, 72, 74-75, 103, published by Intraop Medical Corporation.

Mobetron® 1000 Product Specifications, A210431L (Jun. 2009), p. 5, published by Intraop Medical Corporation.

Ma, "Dosimetric properties of magnetically collimated electron beams for radiation therapy", Med. Phys. 31(11), Nov. 2004, pp. 2973-2977.

Brochure for Elekta SL Family of Products, Philips Medical Systems, 1987.

* cited by examiner

METHOD AND SYSTEM FOR ELECTRON BEAM APPLICATIONS

BACKGROUND OF THE INVENTION

Approximately 1.4 million Americans each year develop skin cancer. The standard regimen for this disease is generally either surgery to remove the lesion and a small amount of surrounding normal tissue, or radiation. The standard dose of radiation is 50 to 60 Gy, delivered in 15 to 30 fractions of about 2.0-3.3 Gy per fraction, to eradicate the lesion through radiation destruction. Both surgery and radiation have similar outcomes. Surgery is often the treatment of choice for skin lesions because the surgeon can, in a single session, remove areas of tissue adjacent to and below the lesion to ensure that the entire lesion has been removed. However, if the skin lesion is located on a cosmetically challenging area, where a scar might form and be visually distracting, or if removal of the lesion would result in removal of tissues that would create a visible deficit, such as a nostril, eye lid or ear lobe, thereby requiring subsequent cosmetic surgery to restore the appearance of the patient, radiation is generally a preferred alternative to surgery.

Additionally, radiation is often the preferred method of treatment for the lower extremity in elderly or diabetic patients. These patients often have vascular insufficiency leading to delayed healing and infection after surgery. Furthermore, patients who opt for irradiation of skin cancer have a non-invasive treatment option.

Generally, patients seeking radiation treatment for skin cancer are irradiated in cancer centers by using 1) the electron beams from an electron linear accelerator that is capable of producing multiple x-rays as well as multiple electron energies, or 2) x-rays (often at energy levels of 50 to 300 keV) that are produced by orthovoltage or superficial x-ray equipment. Both types of equipment require that the patient be irradiated in a shielded room. While both modalities may be used for irradiation of skin cancer, many clinicians feel that electron beams provide for more homogeneous dose distributions and less damage to underlying structures, and are therefore the preferred modality for skin cancer irradiation applications.

Another well-known use of electron beam radiation is in the treatment of invasive cancers. Such cancers include neck nodes in head and neck cancer. Additionally, electron beam radiation may be used as a boost in the treatment of breast cancer.

When skin cancer or invasive cancer is to be irradiated, the radiation is generally delivered in a cancer center. A cancer center is a hospital-based or free-standing radiation therapy facility that uses high energy x-ray or high energy electron beam radiation to treat cancer patients, generally on an outpatient basis. At a cancer center, radiation is produced by linear accelerators that generally weigh several tons (often 7 to 10 tons) and require tons of concrete shielding to contain stray radiation. Thus, cancer centers are almost always located in the basement or ground floor level of a hospital or facility. Cancer centers treat both a) patients with invasive cancers and b) those with superficial cancers, such as skin cancer.

For electron irradiation of skin cancer, typically 15 to 30 fractions of electrons at energies of 6 to 9 MeV are required. For electron treatment of invasive cancer, typically 5 to 20 fractions of electrons at energies of 6 to 15 MeV are required. For invasive cancer, typically 90% of all electron energies used are 12 MeV or lower. Energy control is important in the irradiation of skin lesions because the energy of the incident electron beam is directly related to the depth of penetration of the radiation into the patient. The generally accepted standard for irradiation of humans is that the energy be controlled to at least ±5% with ±3% being more desirable.

Many current radiation therapy devices that produce electrons have an accelerator guide mounted substantially horizontally (parallel to the floor) and use a magnet at the exit of the accelerator guide both to bend the beam into the irradiation plane and to select the appropriate electron energy for irradiation. For one example of such a system, see FIG. 1 of U.S. Pat. No. 4,987,309, issued Jan. 22, 1991. In such systems, the bending magnet is a source of x-ray generation and creates substantial stray radiation. In fact, the bending magnet employed to select the energy that is desired for the irradiation is generally the principal source of stray radiation in conventional accelerators that operate in the electron mode. The energy-defining slits in the magnet produce much radiation, as do adjustable collimators that define the field size. These bending magnet systems are thus unsuitable for use in unshielded or substantially unshielded environments. Thus, a substantially shielded facility is required when a conventional linear accelerator is used to provide multi-energy treatments.

The amount of required protective shielding for a typical bending magnet system operating only in the electron mode has been estimated by some to be the equivalent of a foot of heavy density concrete surrounding the system (e.g., in the walls of the treatment room, the floor and the ceiling). Sometimes such shielding can require as much as 24 to 60 inches of reinforced concrete if the unit is intended to produce both electrons and x-rays for treatment. See e.g. U.S. Pat. No. 6,422,748. In some prior art accelerator designs that do not use bending magnets, the ambient stray radiation will be substantially reduced. However, where a beamstopper is not used, approximately 1 to 1.5 tons of movable shielding must generally be positioned about the patient prior to treatment. This shielding is placed 1) laterally about the patient to protect those outside the room from scattered radiation, and 2) below the treatment table to protect those on the floor below. The shielding is placed so as to comply with current radiation exposure standards for the operation of radiation devices.

Electron linear accelerators have been also developed for delivering intraoperative electron beam radiation therapy (IOERT) in unshielded operating rooms. These systems are designed to operate only in the electron mode and require little additional shielding. One such device, sold by Intraop Medical Corporation of Sunnyvale, Calif. under the product name Mobetron 1000, would be suitable for use with the current inventions. Similar intraoperative electron beam systems and facilities are described in U.S. Pat. No. 5,321,271, issued Jun. 14, 1994, the entire disclosure of which is incorporated herein by reference.

Other IOERT units have high dose per pulse operation, and are therefore not as suitable for applications that require a low dose per treatment. Furthermore, these units use microwave power variation only to change energies. It is difficult to achieve the ±5% energy control desired for applications of the instant invention when using such a method for energy variation. Some of these other IOERT units are designed to use 80 to 100 cm-long applicator cones. The size of these cones may make their use for the instant invention impractical. Finally, these units generally require the use of mobile shielding to operate within allowed radiation exposure limits in an unshielded environment.

Irradiation of skin cancer may be accomplished at a facility with a conventional electron linear accelerator, similar to the ones used in cancer centers. These devices, however, generally require a heavily shielded concrete vault to protect personnel from stray radiation. Installation or construction of a concrete vault weighing several tons, and the space occupied by such a radiation vault is impractical for smaller facilities, such as most dermatology practices.

SUMMARY OF THE PRESENT INVENTION

A patient with skin cancer is usually seen first by a dermatologist who directs the patient's course of treatment. The course of treatment often involves a surgical technique or a referral to a cancer center. The course of treatment may include irradiation of the skin cancer for cosmetic effect (e.g. to eliminate the need for scarring surgery) and irradiation of the skin cancer for therapeutic purposes. Because lesions on the skin or patient surface are visible, such irradiation treatment also allows the physician to diagnose and evaluate the progress and effect of the irradiation on a daily or weekly basis. In this manner, the invention may be useful in diagnostics.

It is an object of the invention to provide systems and methods for enhancing the irradiation of skin cancer by making it possible to provide irradiation in small facilities such as at a dermatology or other doctor's office, rather than requiring irradiation at a cancer center or hospital. This would allow the skin cancer patient's primary care physician (e.g., the dermatologist) to more readily manage the patient during the course of irradiation.

It further is an object of the invention to provide systems that may be located in a centralized office facility and shared by several doctors.

It even further is an object of the present invention to provide systems that may be installed at other types of facilities (e.g., a cancer center) in an unshielded room.

It also is an object of the invention to provide systems and methods that may be used to provide electron beam irradiation for patients with invasive cancer for which this modality is preferable as part of the irradiation regimen.

Another object of the invention is to provide systems and methods that may be used to provide electron beam irradiation at varying energy levels, without the need for additional complex or expensive electronics or microwave components.

An additional object of the invention is to provide systems and methods that may be used to provide electron beam irradiation to comply with current radiation standards and with current limits on radiation exposure to surrounding areas.

It is an object of the present invention to provide electron linear accelerator methods and systems to comply with international radiation safety standards that are mandated in the design of electron linear accelerators.

These and other objects of the present invention may be accomplished by providing systems and methods for providing electron beam irradiation at varying energy levels, without the need for additional complex or expensive electronics or microwave components.

The present invention generally encompasses electron beam generation systems and methods that provide an electron beam with little of the stray radiation associated with conventional electron beam generation systems. Systems and methods of the invention generally comprise an electron gun, a linear accelerator, an applicator, and a moderator. The moderator may be comprised of at least one low-z material with an atomic number above 4.

Low-z materials have a relatively lower atomic number (in this application, less than or equal to 40). Low-z materials degrade the energy of the electron beam incident on the surface of the low-z material, so that the energy of the electron beam exiting the low-z material is lower. The lowest-z element that is possible to use in such systems is beryllium (atomic number 4). But beryllium may be toxic in such systems, so the moderator may be comprised of a low-z material with an atomic number above 4 to avoid the problem of toxicity.

The path of the electron beam striking the surface to be irradiated may be substantially collinear with the path of electron travel within the linear accelerator. In some embodiments of the invention, the path of electron travel may be closer to vertical than horizontal, such that the largest portion of any stray radiation is directed in the direction of the floor of the treatment room, such that the floor and ground absorb enough of the radiation that substantial room shielding is not necessary.

In one embodiment of the invention, skin lesions (including skin cancer) may be irradiated while the patient is in a substantially unshielded room.

In another embodiment of the invention, moderators comprising an acrylic material may also be placed in the path of an electron beam to inexpensively reduce the energy level of the electron beam.

Further embodiments of the invention are described below.

DETAILED DESCRIPTION OF THE INVENTION

A detailed description of preferred embodiments of the invention may be found below. Such embodiments are exemplary, and one skilled in the art will recognize that that it may be possible to practice the methods and build the systems of the present invention without strict adherence to the embodiments described herein.

A number of interrelated design elements should be considered when placing a multienergy electron accelerator into an unshielded environment to treat skin cancer or invasive cancer, provide cosmetic results, or provide diagnostic doses with electrons. These design elements include:

1) Providing sufficient electron beam energies to meet various penetration and dosage requirements;
2) Providing means for mounting and moving the accelerator head such that the head may be positioned properly to irradiate the area to be irradiated (e.g., treatment area on a patient);
3) Providing means to shield for the primary x-rays and scatter radiation that are generated by the systems;
4) Providing means for energy control that will not produce significant stray radiation; and 5) Providing a suitable applicator system to direct and focus the radiation from the linear accelerator upon the area to be irradiated (e.g., treatment area on a patient).

These design considerations may be met, in part, by using an X-band microwave accelerator, a conventional S-band accelerator or a C-band accelerator. The use of an X-band accelerator may result in a lower weight device. The lower weight may ease positioning, because less force may be required during positioning and less structural support may be necessary.

It should be understood that the inventions described herein may be practiced with any accelerator, including but not limited to an X-band accelerator, an S-band accelerator (such as those commonly used in medical therapy systems) or a C-band accelerator (such as those being used for some specialty radiation therapy applications). S- or C-band accelerators may increase the weight of the device, yet such a unit would be functional in a small office environment (e.g., a dermatology office) or in an unshielded room in a larger facility (e.g., a cancer center). These units will be functional for many applications in non-sterile environments as well as in sterile environments like operating rooms to conduct intra-operative radiation therapy ("IORT").

Figure 1:
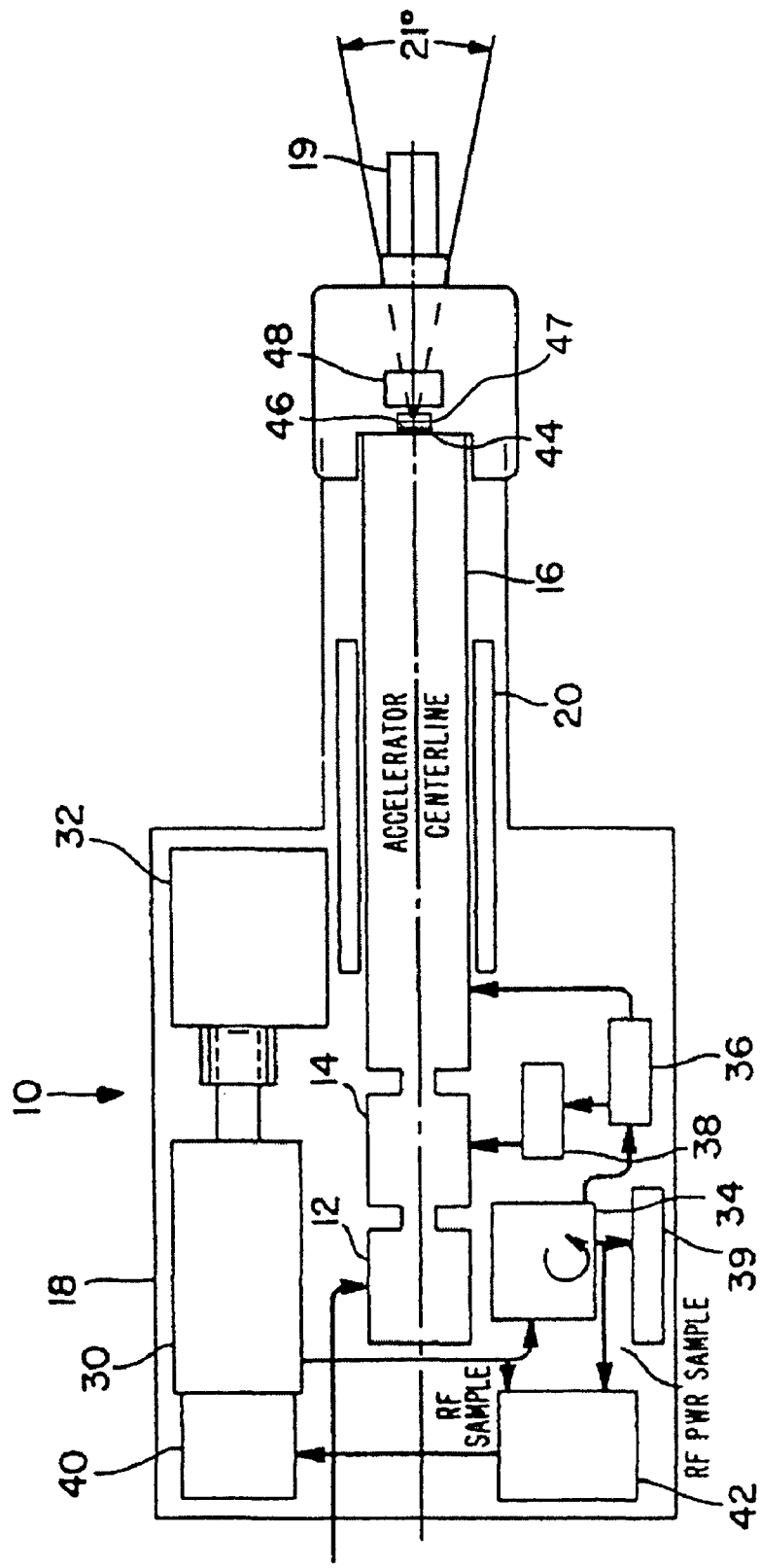
FIG. 1 shows a block diagram of an exemplary set of electron beam generating components that may be used in connection with the invention.

The electron beam source for this electron beam radiation therapy ("EB-RT") system of this invention may be an X-band linear accelerator operating at peak energies of 9 MeV for dermatology applications or at 12 MeV for invasive cancer applications. As shown in FIG. 1, the electron beam source may comprise the accelerator head 10 which may include an electron generating means comprising an electron gun 12 and any beam transport system that might be required to inject the electrons through an opening into the linear accelerator, a prebuncher 14, and a series of standing wave cavities 16 disposed along the centerline of the accelerator head housing 18 containing the accelerator structure.

One example of electron gun 12 has been sold by L3 (formerly Litton) under the product name M593 Electron Gun. The injector cathode of the electron gun 12 operates in some embodiments at 10 to 14 kV and has a very small diameter emitting surface. This design is intended to provide low emittance and good capture efficiency while maintaining low energy spread. The injector may be used in connection with a non-interceptor grid to enable accurate control of the injected current. The grid is considered to provide the advantage that if the electron gun 12 degrades over time, the voltage to the grid may be increased to increase current and appropriate modifications may be made to the electron gun 12 to counteract degradation of the electron gun 12. However, employing a grid is generally considered to be more expensive than use of a non-gridded gun. Other electron gun designs may be used without departing from the scope of the invention. The control of the injected current, mentioned above, allows (1) monitoring the output beam signal and (2) use of a feedback circuit to regulate and adjust the injector current to stabilize the delivered dose of radiation. It is understood that the dose rate may fluctuate over time, so long as the integral dose is stabilized.

IORT procedures using electron beams are called IOERT. For IOERT operation, the patient may be anesthetized and have an open wound, making quick completion of the radiation dose desirable. For irradiation of skin or skin disorders, however, the output level of the electron gun 12 may be reduced, because the total dose is given over many treatments (called "fractions") and the dose per fraction that is needed to treat skin disorders is about ⅛ to 1/10 of the dose delivered during an IOERT application. This reduces the radiation dose rate for a given period of time. Doing so allows for at least a few advantages. A slower dose rate extends the irradiation period, allowing a technologist to take notes or perform other tasks during the irradiation period.

Reducing the radiation dose rate in some embodiments will allow the electron gun 12 to move into a more stable operation cycle for dermatology operation and reduce the percentage of any dosage error. The reduction in output may be accomplished by maintaining the same number of pulses per second to the electron gun 12 but increasing its grid voltage so that fewer electrons per pulse are accelerated thereby reducing the radiation dosage to the desired level. It is a common feature of many electron guns that when operation begins, the first few pulses provide a less controlled dose of electrons. Then, after these pulses, the electron gun 12 reaches relatively stable operation. By reducing the dose per pulse, the number of stable pulses increases relative to the total number of pulses. This is expected to reduce the percentage of any dosage error over systems employing a smaller number of pulses, each of which contains a large dose of electrons.

The electron gun 12 may be offset at an angle from being substantially perpendicular to the ideal plane to be irradiated and a bending magnet may be used to bend the beam into the appropriate path without departing from the scope of the invention, as long as the electron beam path is not bent after it has entered the linear accelerator.

In some embodiments, this invention provides for use of an electron beam system in a substantially unshielded room. Even if the electron beam system is on the ground floor, a beamstopper may be helpful in absorbing radiation scatter, without the need for a substantially shielded room. It may also be useful to use a treatment couch that can be tilted. This may be done in a manner that will reduce need for rotation of the beam path. However, if the electron beam system is positioned both away from a wall and such that approximately the first ±20 or 30 degrees of patient scatter will be absorbed by the floor, the beamstopper may be entirely eliminated without the addition of substantial shielding to the room. Further, depending on the room dimensions, if the center of scatter is less than approximately 3 meters from a barrier or wall, it may be necessary to add insubstantial shielding along the barrier or wall. The height and thickness of the required shielding will, in some embodiments, depend on the distance of the electron beam system from the barrier or wall. The amount of shielding that may be required can be determined based on radiation standards, such as government regulations. If the room is sufficiently large, the unit can be positioned relatively far from all barriers or walls. In such rooms, it may be possible to operate the unit without a beamstopper and without substantial shielding. The amount of shielding required for such operation can be calculated so that the unit complies with state, national, and international requirements for radiation protection.

The dimensions of the initial standing wave cavities 16 may be varied to produce beam bunching, thus reducing energy spread. A solenoid or focusing coil 20 may be placed over the accelerator structure to confine the beam, to thereby improve transmission efficiency and reduce stray x-ray radiation leakage. A titanium window 44 at the beam outlet is used in some embodiments to maintain a vacuum within the accelerator. The window 44 may be formed of other equivalent materials rather than titanium.

A thin scattering foil 46 at the beam outlet may be used to spread the electrons. The electrons may be scattered over a 20 cm diameter field with a maximum of 10% variation in dose rate applied to any region within the field.

Removable applicator cones 19 are disposed in some embodiments between the treatment field and the scattering foil 46, at the beam exit region, to define the shape and size of the treatment field. The applicator cones 19 may be designed to provide additional scattering to achieve improved beam flatness for treatment. For dermatology applications, generally field sizes ranging in diameter from 2 cm to 10 cm may be sometimes required. Final treatment field definition may be accomplished by placing radiation shields (e.g. lead sheets) on the surface to be irradiated (e.g. portion of patient's body to be treated) with a cutout opening that contours the desired treatment area (e.g. a skin lesion) and permits the electron beam radiation to strike the area of the lesion. Alternatively, in some embodiments, the applicator cones 19 should have the ability to provide custom shaping at the distal side of the applicator cones 19. For invasive cancer applications, generally, field sizes of up to 20 cm×20 cm may be required, and custom field shaping from the distal end of the applicator cones 19 may be preferable. For both dermatology and some invasive cancer applications, a gap of approximately 5 cm may be allowed from the distal end of the applicator cones 19 to the surface to be irradiated. This gap allows the center of the treatment field to be a substantially fixed distance from the scattering foil 46 in some embodiments, even though the surface to be irradiated may not be flat. In these applications, a distance indicator and center of the field indicator may be used. In some embodiments either electronic or mechanical indicators are employed.

For certain treatments, applicator cones 19 comprising steel and aluminum may be used. The use of these metals allows for ease of sterilization between treatments in some embodiments, if required, and less leakage of stray radiation. Generally, a steel and aluminum applicator cone 19 may be constructed such that the top portion of the applicator cone 19 (furthest from the surface to be irradiated) comprises aluminum. This may reduce overall weight. The bottom portion of the applicator cone 19 (closest to the surface to be irradiated) may be constructed of steel, to reduce the volume of metal on the sides of the applicator cone 19 that would be required for adequate shielding. This reduction in volume of a steel cone tip may allow an increased area of irradiation with the same outer cone tip circumference than would an aluminum cone tip. For example, an aluminum cone may require a 5 mm thick wall to prevent penetration of radiation, while a steel cone wall 2 mm thick may prevent penetration. If the energy is 9 MeV or less, 2 mm of aluminum may provide adequate shielding, though the shielding may be less than that provided if stainless steel were used. Cones may be constructed from other materials, e.g. plastic or Lucite (Lucite is DuPont's product name for polymethyl methacrylate), especially for external radiation applications. However, radiation transmission through the cones should be considered when choosing such materials.

A primary collimator may be located at the exit end of the accelerator guide and encompass both the scattering foils 46 and an internal monitor chamber. The primary collimator may take the form of a truncated pyramid or truncated cone. The applicator cones 19 may include scattering plates in some embodiments to additionally flatten the radiation beam while still producing relatively low levels of x-rays.

For intraoperative uses, a specially designed tube may be inserted into the treatment area. The tube is intended to prevent healthy tissue from falling into the treatment area in some embodiments. This type of tube may also be intended to maintain a more homogeneous beam throughout the treatment area. It is understood that any particular device constructed according to the principles of the invention disclosed herein may require a special collimator and applicator cone 19 design. The design of an appropriate collimator and applicator cone 19 can be done by empirical iteration or by a Monte Carlo simulation of the device and its operation. Such simulations have been used to design applicator cones 19 with circular openings, and even with rectangular and oblong openings of dimensions 8 cm×15 cm. See, for example, Janssen et al., "Prototyping a large field size IORT applicator for a mobile linear accelerator", Physics in Medicine and Biology, 53 (2008) 2089-2102, which is incorporated by reference herein in its entirety.

As mentioned above, for external (e.g. dermatological) applications, a center of field indicator may be used to indicate the center (or approximate center) of the electron beam upon the surface to be irradiated. Such an indicator may be provided by shining a light through the center of the applicator cone 19 with a reticle lens or mechanical crosshair to indicate the field center. Alternatively, a video camera with a fiber optic light system may be employed. Other indication systems may be employed without departing from the scope of the invention.

The microwave power used to drive the accelerator is generated by a magnetron 30. One such magnetron 30 has been sold by California Tube Laboratory under model number VMX 1100. In some embodiments, the magnetron 30 is capable of operating at a peak power of 1.5 megawatts and 1.5 kilowatts of average power (i.e., at a duty cycle of 0.001). The pulse length of the magnetron 30 may be 4 microseconds. The pulse repetition frequency may vary from 40 to 240 pulses per second.

In some embodiments, the system employs a conventional modulator and power supply using a hydrogen thyratron switching unit to produce 3 MW peak power for the magnetron 30 via a suitable cable and cable connector. Power to the magnetron 30 may be converted from 8-9 kV to 35 kV by a pulse transformer 32 that may be optionally disposed within the accelerator head housing 18 or gantry stand.

In some embodiments for both dermatology and invasive cancer applications, constant microwave power from the magnetron 30, sufficient to generate the maximum output electron energy from the accelerator guide, is transmitted to the accelerator by means of a waveguide via a power splitter 36 and a phase shifter 38 after passing through a four-port circulator 34. Power not absorbed in the accelerator may be shunted into a water-cooled dummy load 39. If the accelerator structure can be made short enough and still achieve the designed maximum energy in some embodiments, it is possible to eliminate the phase shifter 38, and use a more conventional rf-input system, as is well-known to those familiar with the art. A deQing regulation system may be used to maintain a constant pulse level.

If desired, lower energies may be achieved by using moderators 47. Moderators 47 may be made of at least a low-z material above atomic number 4. Moderators 47 may be placed in the beam path to reduce the electron beam energy to a desirable level. For example, if the moderators 47 degrade 3 MeV, an accelerator may be operated at a single power level of 9 MeV, yet by inserting or removing the moderator 47, differing energy levels of either 6 MeV or 9 MeV may be achieved. One such single element moderator may include carbon. Similarly, a composite of aluminum and beryllium may be used. The use of higher-z moderators is possible in some embodiments, but will increase the generation of Bremsstrahlung radiation.

Figure 6:
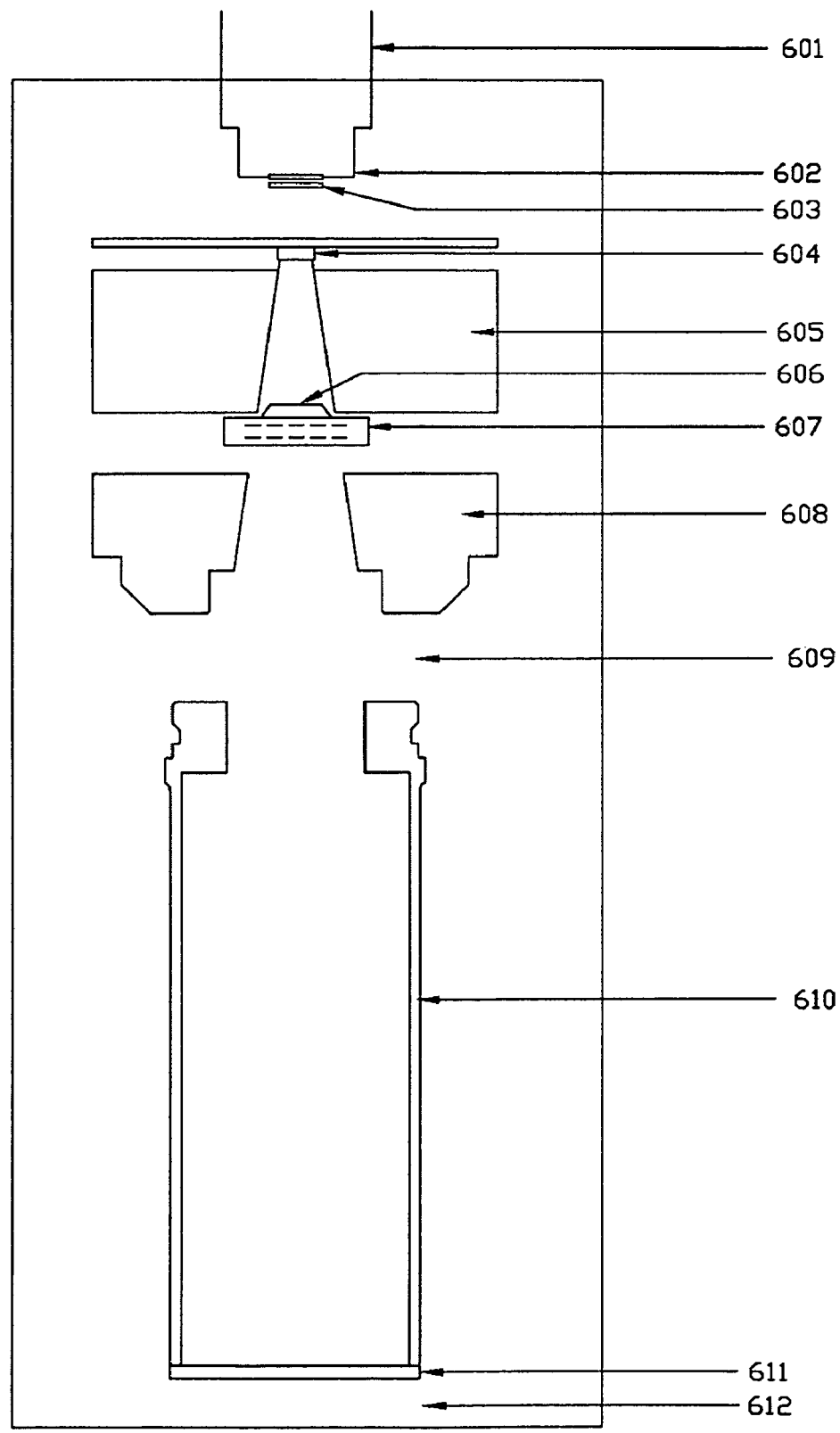
FIG. 6 is a schematic representation of a typical exit beam path from an electron linear accelerator showing the elements in that beam path including the interposition of energy moderators.

The energy moderator 47 can be located in a number of possible positions and still provide effective energy attenuation. FIG. 6 shows a schematic representation of the exit beam path from an electron accelerator utilizing an energy moderator. Electrons may leave the exit window 602 of the accelerator 601 and strike the primary electron beam scattering foil system 603. The method to optimize the design of the primary electron beam scattering foil system 603 can be done through empirical iteration or through Monte Carlo simulation. In some embodiments, the materials, dimensions, and shape of the primary scattering foil system 603 will depend on the location of the primary scattering foil system 603 in the exit beam path, and the geometry and materials used in the primary collimators 605 and 608, the materials and thickness of the ion chamber or dose chamber enclosure 607 as well as the materials and thickness of the collection plates used in the ion chamber or dose chamber, and the material, diameter, and design of the electron applicator 610. The energy range of the incident electron beams, the presence of air gaps 609 between the primary collimator 608 and the electron applicator 610, and between the distal end of the electron applicator 610 and the treatment surface 612 will all impact the design of the primary scattering foil system 603 in some embodiments.

The scattering foil system 603 serves two functions in some embodiments: It will broaden the electron beam that emerges from the accelerator window 602 from approximately a 2 mm diameter to a conical shaped beam with a half angle that depends on the foil material and thickness and the incident energy distribution of the electron beam. The second function of the scattering foil system 603 may be to help shape or flatten this distribution of energies over the field size range needed for the clinical application. Generally scattering foil system 603 may employ two separate foils. The first foil will scatter the beam and the second foil will help flatten the beam in some embodiments. The distance between these two foils can vary, depending on the energy range of the unit, the field size needed for the treatment application, and the geometry and materials of the mass elements in the treatment head. In some systems, in order to achieve adequate flatness of the treatment beam, multiple scattering foils may be employed. Generally, electron scattering foils may be designed using empirical iterations or Monte Carlo simulations.

Notwithstanding the suggestion to use dual scattering foils, alternative methods known to spread the electron beam homogeneously may be used, such as raster scanning or using air scatter and longer applicator cones to provide greater path lengths. For example, air column scatter within the electron applicator 610 may be used to flatten the electron beam after the beam passes through a moderator. The implementation of these alternative methods or variations of their implementation do not depart from the teaching of this design.

The energy moderator can be located in a number of positions, but should be located distally to the scattering foil system 603 to achieve the best results in some embodiments. The closer the energy moderator is to the scattering foil system 603, the smaller its diameter can be. So, a moderator positioned closer to the scattering foil system 603 should, in some embodiments, have a significantly smaller diameter than a moderator located further away, such as at position 606. For example, a moderator 10 mm from the scattering foil system 603 may have a diameter of 10-20 mm to provide it with a sufficient safety margin to encompass a beam 3-4 mm in diameter. A moderator located further from the scattering foil system 603, such as at position 611 at the distal end of the electron applicator 610, may have a larger diameter. The diameter of the moderator may be determined by measuring the diameter of the beam. The diameter of the moderator should, in some embodiments, be 6-10 mm larger than the diameter of the beam.

In some embodiments, the thickness of the moderator needed to degrade the energy is, to first order, independent of the location. The energy moderator will, in some embodiments, result in a decrease in output of the emerging beam. If the accelerator 601 provides sufficient beam output, a reduction in output by the moderator may not be significant.

If output reduction is of sufficient concern, then a composite moderator can also be designed using a combination of low- and high-z elements. In this application, high-z elements have an atomic number greater than 40. This may have the advantage of making the resulting moderator thinner than if only a low-z element was used and thus may make its insertion into the beam path easier to accomplish. However, the trade-off in using higher-z elements in the moderator is that the Bremsstrahlung radiation of the resultant beam will be increased in some embodiments. This may not be clinically significant provided that the resulting Bremsstrahlung radiation is within clinically acceptable limits.

The presence or absence of the moderator in the beam path should be automatically indicated by radiation interlocks in some embodiments when the desired energy in use is selected. Radiation interlocks should make it impossible to enable irradiation if the moderator is not properly positioned. This may ensure that international radiation safety standards that are mandated in the design of electron linear accelerators are complied with.

For example, the energy selected will be different depending on the different penetration desired for different patients. To achieve the different energies, the moderator may be used. If the moderator is positioned above the collimator or ion chamber, the moderator may not be visible to the operator. Thus, a failsafe mechanism may be useful. If the energy is selected and the moderator is not properly positioned, the failsafe mechanism must make it impossible to enable the irradiation. This is because the failure of the moderator to come into position properly can result in a significant overdose of radiation. Mechanisms of radiation interlocks for moderators may be similar to those in accelerator systems that employ moveable electron scattering foils.

A second, easily accommodated position for energy moderation in some embodiments is at the very end of the electron applicator 610 (position 611 of FIG. 6). In this location, the best material to use may be an acrylic. Up to 20 MeV, for every 5 mm of acrylic used, the energy is degraded by approximately 1.5 MeV in some embodiments. Because of the relatively low z-value of acrylic, there is little increase in x-ray contamination in some acrylic embodiments. Furthermore, since this position is readily visible to the operator, and since the proper attachment of the moderator to the electron applicator 610 can be designed to be failsafe and automatically indicated as described above, interlocking a moderator in this position may not be required.

A combination of an internal moderator of sufficient thickness to reduce the emerging beam energy by 1.5 to 3 MeV, together with an external acrylic moderator, provides significant flexibility in energy selection while simplifying the accelerator design by operating the unit at a single energy in some embodiments. For example, if one operated a linear accelerator 601 at a single energy of 12 MeV, an internal moderator could be used either in position 604 or position 606 of FIG. 6, to reduce the energy to 9 MeV, and a secondary moderator located at position 611 could be used to reduce the energy further to 6 MeV. Similarly, a linear accelerator designed to operate at a single energy of 9 MeV can have a combination of internal and external moderators that provide clinical treatment energies ranging as low as 3 MeV.

Systems with different geometries may require different materials and positioning to achieve optimal radiation distributions to treat patients. Optimization of the system can be made through experimentation and trial and error, but can also be achieved "a priori" by use of Monte Carlo computer reconstruction to accurately predict the performance of the beam.

For some embodiments, the exit window 602 of the accelerator guide is made of 0.0015 cm titanium. The scattering foil system 603 may use 0.0025 cm of tantalum followed by a conically shaped aluminum flattening filter with an altitude of 1 mm, to absorb electrons of higher energy, as discussed above. The thickness of the moderator needed to degrade the energy may also be dependent on the location. For an accelerator 601 operating at 9 MeV, an internal moderator consisting of 7 mm of graphite or 5 mm of diamond located at position 604 of FIG. 6 may attenuate the beam by about 3 MeV. (Thinner moderators of graphite may result in less energy attenuation). The addition of an external moderator at the end of the electron applicator 610 at position 611 in FIG. 6, consisting of 5 mm of acrylic, will reduce the energy to about 4.5 MeV in some embodiments. If 10 mm of an external acrylic moderator was used, it would reduce the energy to about 3 MeV in some 10 mm acrylic embodiments. If the internal moderator is not in position, then the external moderators of 5 mm and 10 mm will produce energies of about 7.5 MeV and 6 MeV, respectively, in some embodiments. Alternatively, a composite internal moderator in position 604 of FIG. 6, consisting of 3 mm of beryllium and 3 mm of Aluminum, would have about the same energy reduction of 3 MeV in some composite embodiments. Various combinations of materials that could be used in the internal moderator so as to achieve the desired energy reduction can be designed by using a combination of materials based on their well-known stopping powers for electron radiation.

Another advantage of the use of an energy moderator to provide lower energies is that in some embodiments, the electron gun current needed to generate a particular output (electron flux) at lower energies will be less with the beam moderator method than with any other approach used to generate lower energy beams such as power variation, using an energy switch, or using a power splitter. In these other multi-energy approaches, the injected electron beam current into the guide is usually greater the lower the output energy desired. For example, in a multi-energy linear accelerator, if the 12 MeV electron beam has a typical gun current of 100 ma needed to generate the desired output, a 4 MeV beam from that same system might require a gun current of 800 ma, and a 6 MeV beam would have a current of about 400 ma. With the energy moderator approach, the gun current may be set for the maximum output energy, which is also the lowest injected electron gun current, and the lower energies may be generated by the moderator techniques described above but still using the same gun current as the maximum energy. The outputs (electron fluxes) at all energies will be approximately the same in some energy moderator embodiments.

Thus, operating at a lower gun current may not only extend the lifetime of the electron gun, but should also reduce the ambient leakage radiation for some multi-energy units. National and international regulatory requirements on radiation devices require that they be housed in a room such that non-radiation worker personnel in surrounding rooms receive less than 20 µSieverts exposure per week. If the ambient radiation from a radiation unit is too high to meet this regulatory requirement, additional shielding must be added to the walls and floor and ceiling to bring the measured radiation in the surrounding areas into compliance. This can result in substantial cost to the facility. A reduction in the ambient leakage radiation can result in lower shielding requirements, for both the electron accelerator, and the room in which the accelerator is housed. This is of special importance for radiation applications that are designed to be used in rooms that are not shielded specifically for radiation units.

Variations to the preferred embodiment in selection of different materials, positioning geometry of the system elements, and thickness of materials, can be done through empirical iterations or Monte Carlo simulations.

Alternatively, energy control may be achieved using an energy switch in a single guide. The energy switch may have one or more positions of operation, with each position resulting in an electron beam of different energy and narrow energy spread.

Alternatively, energy may be changed by load-line variation. Such changes suggest due care to assure that the power level used to achieve the desired energy is sufficiently stable and is interlocked to achieve a well-defined output energy.

Figure 4:
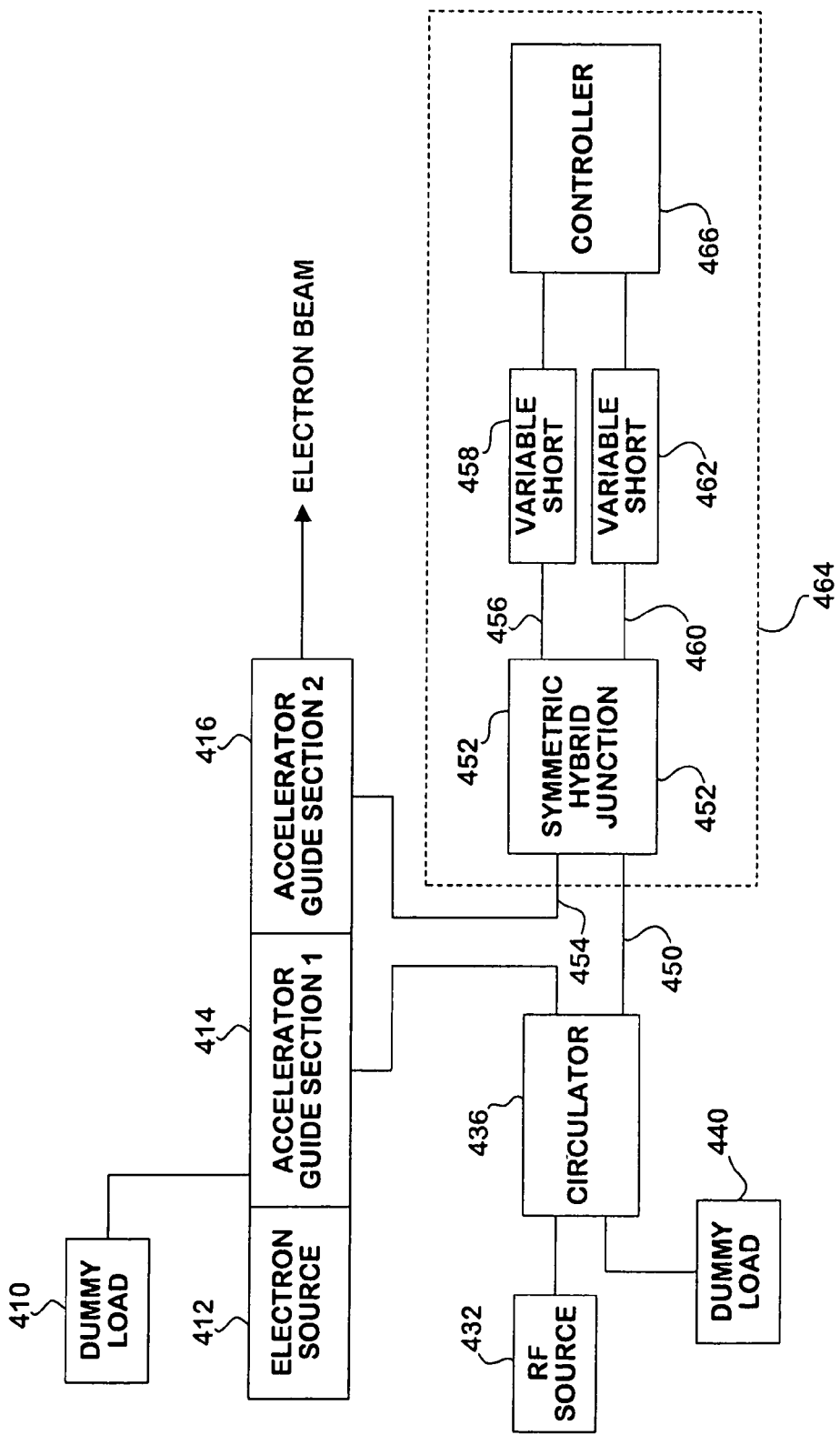
FIG. 4 shows a block diagram of exemplary components that may be used to control energy with two collinear accelerator guides.

FIG. 4 shows another possible manner to achieve energy control through the use of an electron source 412 with two collinear accelerator guides 414 and 416 and a power splitter 464, one example of which is described in U.S. Pat. No. 5,661,377, issued Aug. 26, 1997, the disclosure of which is incorporated herein in its entirety. Sufficient microwave power to achieve a lowest desired energy may be injected by RF Source 432 into the first accelerator guide 414, passing through a 4-port circulator 436 and a power splitter 464. The power splitter 464 may include ports 450, 454, 456, and 460, symmetric hybrid junction 452, variable shorts 458 and 462, and controller 466. Excess power not needed for the lowest energy may be diverted by the circulator 436 to a water-cooled dummy load 440. Reflected power from the first accelerator guide 414 may be shunted into a second water-cooled dummy load 410. To achieve higher energies, additional power may be injected into the second guide 416 by the power splitter 464. Coherent operation and energy control may be achieved by the use of phase shifters (e.g. variable shorts) 458 and 462 that ensure that the phase of the microwave power in the second guide 416 is matched (e.g. identical) to the phase of the microwave power in the first guide 414. Excess power from the second guide 416 may be shunted to a water-cooled dummy load (not shown).

The resonant frequency of the magnetron 30 in FIG. 1 may be matched to the accelerator to enhance (e.g. optimize) the system operation. This may be achieved by using a tunable magnetron with the tuner driven by a stepper motor 40. The stepper motor 40 may be controlled by an automatic frequency control system 42 which detects phase variation between the forward and reflected power applied to the accelerator, thus forming a tracking system to maintain enhanced (e.g. optimum) operation irrespective of temperature or load changes.

A transmission ion chamber 48 at the beam outlet may be used to monitor dose rate and integral dose. The transmission ion chamber 48 may be made of plastic elements coated with a thin metallised layer to minimize production of Bremsstrahlung x-rays.

The scattering foils 46 and transmission ion chamber 48 may be encased within a tungsten or lead collimator to limit the field size to the maximum needed for the application.

Figure 3:
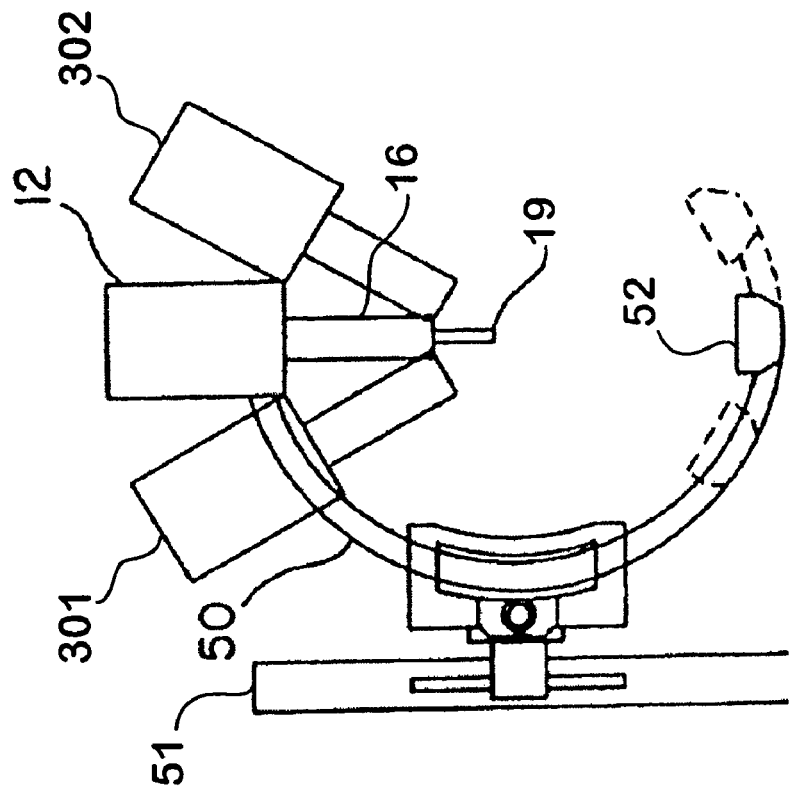
FIG. 3 shows a side view of an exemplary electron beam generator mounted upon an exemplary mechanical support.
Figure 2:
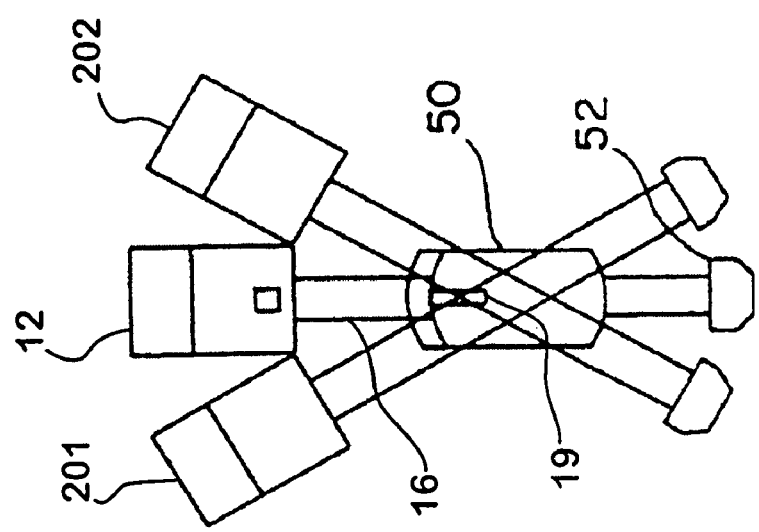
FIG. 2 shows a front view of an exemplary electron beam generator mounted upon an exemplary mechanical support.

The accelerator head housing 18 may be mounted to a mechanical support or C-arm, that can rotate the accelerator head housing 18 about a human or animal that is positioned for irradiation (e.g., on an irradiation table or sitting in an irradiation chair). In some embodiments, the structure or C-arm will provide rotation in at least two axes for maximum flexibility. Minimum rotation of ±45 degrees about the X-axis may be required. Rotation of ±30 degrees about the Y axis may further facilitate the positioning of the unit. In addition, the accelerator head 10 (i.e. movement along the Z-axis) may be vertically adjusted. (In defining the axes above, the Z-axis may be collinear with the path of the electron beam as it strikes the surface to be irradiated.) FIGS. 2 and 3 show one exemplary configuration of electron gun 12, accelerator guide 16, applicator cone 19 and an optional beam stopper (or counterweight) 52 mounted on a mechanical support 50 to a wall (not indicated in FIG. 2). It is understood that in the description that follows electron gun 12 and accelerator guide 16 are both rigidly attached to each other, and are in the same accelerator head housing.

Electron gun 12 and accelerator guide 16 (the principal elements contained the accelerator head housing) plus the applicator cone 19 may be oriented downward as shown in FIGS. 2 and 3. The electron gun 12 may be collinear with the accelerator guide 16, or it may be at a fixed or variable entry angle to the accelerator guide 16. In this way, the electron gun 12 and accelerator guide 16 forms the system that is being rotated. Positions 201 and 202 indicate rotation of the principal elements of the accelerator head housing (electron gun 12 and accelerator guide 16) plus the applicator cone 19 and the optional beam stopper (or counterweight) 52 about the X-axis. FIG. 3 shows a different view of the same configuration of the principal elements of the accelerator head housing (electron gun 12 and accelerator guide 16), applicator cone 19 and an optional beam stopper (or counterweight) 52 mounted on a mechanical support 50 to a wall 51. Positions 301 and 302 of the principal elements of the accelerator head housing (electron gun 12 and accelerator guide 16) plus the applicator cone 19 and optional beam stopper (or counterweight) 52 indicate rotation about the Y-axis.

Figure 5:
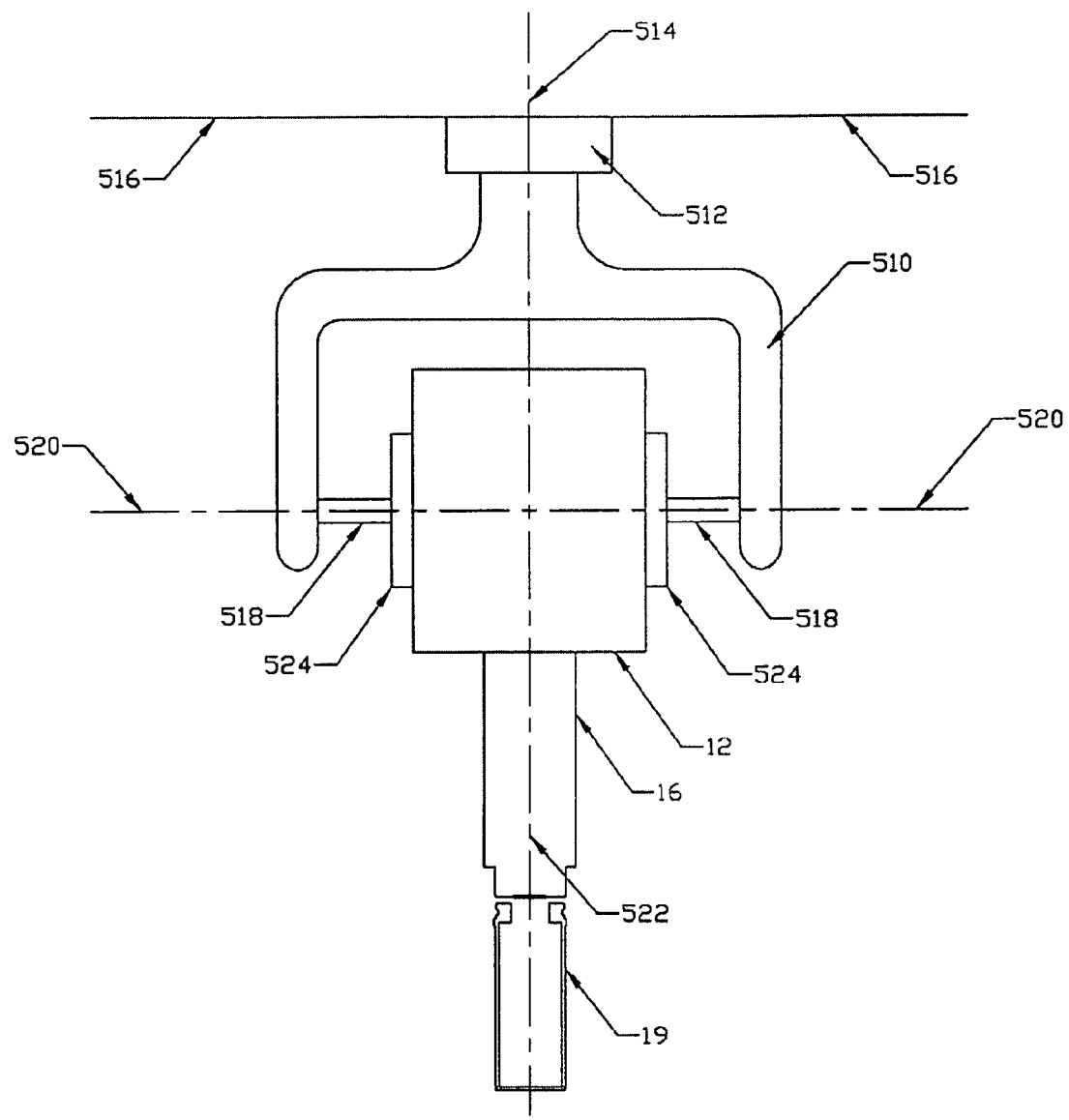
FIG. 5 shows a view of an exemplary mechanical support for use with an electron beam generator that may be used in connection with the invention.

Alternately, the housing may be mounted on a gimble or yoke arrangement that attaches to the ceiling, wall, or floor and has sufficient rotational and vertical articulation to be positioned about a human or animal for irradiation (e.g., on an irradiation table or chair). One example of such a yoke is depicted in FIG. 5, which shows electron gun 12, accelerator guide 16, and applicator cone 19 mounted on surface (e.g. a wall or ceiling) 516 by yoke 510. Mechanical attachment 512 allows rotation of the yoke 510 about axis 514. Axis 522 depicts the path of the electron beam. The default position for axis 522 may be collinear with axis 514. However, it is more likely that the default position of electron gun 12 is such that the plane formed by axes 520 and 522 is perpendicular to axis 514 in some embodiments. Mechanical attachments 518 may allow for rotation of electron gun 12 about axis 520. Mechanical attachments 524 may allow for movement of electron gun 12 along axis 522. It will be understood that the depicted configuration may result in displacement of the electron beam from the area for irradiation when, for example, electron gun 12 is rotated about axis 520 or certain other rotations are performed. This may result in the need to reposition the irradiation area whenever such rotations are performed. Alternatively, a more complex yoke 510 may be constructed which allows for the electron beam to remain directed at a specific area even when electron gun 12, accelerator guide 16, and applicator cone 19 are rotated to provide radiation from a different angle.

In most applications, it is important in the design of the system to limit (and if possible, minimize) stray radiation emanating from the accelerator structure or its elements. For example, the accelerator structure may be encased in a lead and steel support housing to minimize radiation leakage from the accelerator guide. The steel support may also serve as a magnetic shield to shield the electron beam in the accelerator guide from stray or ambient electromagnetic radiation fields. Even if all sources of accelerator leakage are eliminated, when the electrons strike a human or animal subject during irradiation they will inevitably produce "patient"-generated Bremsstrahlung scatter in some embodiments. Fortunately, in most embodiments, this patient-generated scatter is in the forward direction. For some embodiments where irradiation is delivered in the vertical or near vertical direction, most of this patient-generated scatter will be directed into the floor. However, if it is necessary to angle the radiation device, stray radiation levels might exceed regulatory limits (or, where regulation is lax, safe limits) in adjacent rooms. To reduce this possibility, a beam stopper of sufficient lead thickness (e.g., approximately 8 inches thick) may be mounted opposite the accelerator head housing to intercept the primary radiation produced by the scattering foil and collimator, as well as most of the patient generated scatter. This allows installation of the accelerator in most unshielded environments (e.g., small offices, mobile environments, and temporary structures) without the need to provide additional shielding. Where the accelerator is installed in a facility on other than the ground floor, shielding in the floor may be necessary.

An alternative embodiment, which may be used independently or in conjunction with the above embodiment, provides for a patient-positioning device (e.g. an irradiation table or chair) that may be tilted ±20 degrees. This may be similar to features found in many operating room tables. By using the tilt capability and properly positioning the patient for irradiation (e.g., on the table), most irradiation may be given in a near vertical position, thereby eliminating the need for a beam stopper in ground floor installations.

Where additional shielding is needed, a barrier of lead (approximately 1 cm thick by approximately one meter high) may be used to protect adjacent areas of the building. Where the accelerator is mounted in a floor above the ground floor, the floor may be shielded with steel plates of the appropriate thickness to prevent radiation from passing through.

An alternative embodiment may provide for multiple energies achieved over multiple fields of application.

While preferred illustrative embodiments of the invention are described above, it will be apparent to one skilled in the art that various changes and modifications may be made therein without departing from the invention.

What is claimed is:

1. A system comprising:
   an electron beam source for generating an electron beam using a linear accelerator;
   said electron beam source and said linear accelerator being positioned to generate an electron beam;
   an applicator constructed appropriately to physically define one or more of shape, size, and flatness of said generated electron beam, wherein said applicator is positioned such that said generated electron beam will exit said applicator substantially collinearly to said electron beam source; and
   a moderator mountable in a path of said generated electron beam, such that if said moderator is mounted in said path, said generated electron beam will emerge from the system with a lower energy level than if said moderator is not mounted in said path, wherein said moderator comprises at least an element above atomic number 4.

2. The system of claim 1, further comprising at least one additional moderator being mountable in the path of said generated electron beam,
   wherein if a plurality of said moderators are mounted in said path, said generated electron beam will emerge from the system with a lower energy level than if a single moderator is mounted in said path.

3. The system of claim 2, wherein said moderators will reduce the energy level of said generated electron beam by an amount in the range 2 MeV to 12 MeV if said moderators are mounted in said path.

4. The system of claim 1, wherein said moderator is mountable distally to a scattering foil system.

5. The system of claim 1, wherein said moderator will reduce the energy level of said generated electron beam by an amount in the range 1 MeV to 6 MeV if said moderator is mounted in said path.

6. The system of claim 1, wherein said applicator is mechanically attached to a support such that the applicator is maintained at a predetermined location from an end of a housing containing the electron beam source and the linear accelerator.

7. The system of claim 6, wherein said predetermined location of said applicator is in the range of 0 cm to 10 cm from said end of the housing containing the electron beam source and the linear accelerator.

8. The system of claim 1, wherein operating said electron beam source at a lower current with said moderator in said path of said generated electron beam achieves an equal energy as operating said electron beam source at a higher current without the moderator in the path of the generated electron beam.

9. The system of claim 1, wherein at least when operating at a lower energy, ambient leakage radiation is lower with said moderator in said path of said generated electron beam than if said moderator is not mounted in the path of the generated electron beam.

10. A method comprising:
generating an electron beam with an electron beam source;
physically shaping said electron beam with an applicator, wherein the applicator is collinear with the electron beam source and an accelerator guide;
placing at least one moderator comprising at least an element above atomic number 4 in a path of said beam before said beam irradiates a portion of a patient, wherein said at least one moderator reduces the energy level of said beam; and
irradiating said portion of said patient with said electron beam, while said patient is within a substantially unshielded room.

11. The method of claim 10, wherein the portion of said patient comprises a skin lesion.

12. The method of claim 10, further comprising:
flattening said electron beam before said beam irradiates said portion of said patient.

13. The method of claim 10, wherein said patient is a human or animal.

14. The method of claim 10, wherein
said electron beam passes through an applicator,
said applicator performs at least a portion of said shaping,
said applicator comprises an end positioned closest to said patient from which said beam emerges, and
said end is positioned between 0 meter and 1 meter distant from said portion of said patient.

15. The method of claim 14, wherein said end is positioned between 0 cm and 10 cm distant from said portion.

16. The method of claim 14, wherein said applicator is mechanically attached to a support such that a gap is maintained between the applicator and an end of an electron beam source from which said generated electron beam will exit.

17. The method of claim 14, wherein said at least one moderator is placed at said end of said applicator.

18. The method of claim 14, wherein proper attachment of said moderator to said applicator is ensured by a failsafe mechanism.

19. A method comprising:
generating an electron beam with an electron beam source;
physically shaping said electron beam with an applicator, wherein the applicator is collinear with the electron beam source and an accelerator guide;
placing at least one moderator comprising a composite of at least two different elements in a path of said beam before said beam irradiates a portion of a patient, wherein said at least one moderator reduces the energy level of said beam; and
irradiating said portion of said patient with said electron beam, while said patient is within a substantially unshielded room.

20. The method of claim 19, wherein said at least two different elements comprise at least two low-z moderator elements.

21. The method of claim 19, wherein said at least two different elements comprise at least one low-z element and at least one high-z element.

22. A treatment system for irradiating a patient with variable electron energy, comprising:
an accelerator head including an accelerator head housing, an electron linear accelerator and an electron beam source, wherein the electron linear accelerator and the electron beam source are mounted in said housing, and wherein an electron beam may be generated by the electron beam source and injected in the linear accelerator at an entrance opening, wherein the electron beam may be accelerated by the electron linear accelerator to a higher electron energy and exit the linear accelerator at an exit opening opposite to the entrance opening;
a window for separating a vacuum inside the linear accelerator from atmosphere and allowing the electron beam to pass through the window when the electron beam exits the linear accelerator;
means for expanding the electron beam downstream from the electron linear accelerator to simultaneously irradiate an area substantially larger than a cross-section of the electron beam passing through the window,
a removable electron applicator arranged substantially collinearly with the linear accelerator and the window such that the electron beam will follow a straight line from the linear accelerator to the patient, and wherein the applicator is for physically confining the electron beam and defining a field for irradiation,
a controller for controlling one or more operating parameters of the electron beam source and the electron linear accelerator and for operating the electron linear accelerator at a predetermined electron peak energy,
at least one energy moderator that may be selectively mounted in a path of the electron beam downstream from the linear accelerator and substantially collinearly with the linear accelerator and the window, wherein mounting the at least one energy moderator in the path of the electron beam reduces the electron energy of the electron beam from said predetermined electron peak energy to a predetermined electron treatment energy which is clinically significantly lower than the electron peak by moderating the electron energy of the electron beam, and
wherein the at least one energy moderator comprises at least an element above atomic number 4.

23. The system of claim 22, wherein said at least one energy moderator may be selectively mounted at an end of the electron applicator where the electron beam exits the electron applicator.

24. The system of claim 22, wherein said composite of at least two elements comprises low-Z material for moderating the electron energy of the electron beam.

25. The system of claim 22, wherein the peak of the predetermined lower energy level is at least 1 MeV lower than the predetermined electron peak energy.

26. The system of claim 22, wherein the window is made of titanium.

27. The system of claim 22, wherein operating said electron beam source at a lower current with the at least one energy moderator in the path of the electron beam achieves an equal energy as operating said electron beam source at a higher current without the at least one energy moderator in the path of the electron beam.

28. The system of claim 22, wherein for a given electron energy of the electron beam irradiating the patient, ambient leakage radiation is lower with said at least one energy moderator in the path of the electron beam than if said at least one energy moderator is not mounted in said path of the electron beam.

29. The system of claim 22, wherein the at least one energy moderator comprises a composite of at least two elements to reduce the electron energy of the electron beam by moderating the electron energy of the electron beam as the electrons pass through the composite of at least two elements.

30. The system of claim 22, wherein the at least one energy moderator comprises at least an additional energy moderator being mountable in the path of said generated electron beam is comprised, wherein said at least one energy moderator and said at least additional energy moderator comprise elements of different atomic numbers to reduce the electron energy of the electron beam by moderating the electron energy of the electron beam as the electrons pass through the different elements of the energy moderators.

31. The system of claim 22,
wherein the system provides at least two clinically significantly different electron treatment energies between 3 MeV and 12 MeV,
wherein the linear accelerator operates at the same electron peak energy for both of said at least two electron treatment energies,
wherein the higher of said at least two electron treatment energies is between 9 MeV and 12 MeV and for operating the system at said higher electron treatment energy the at least one moderator is removed from the path of the electron beam, and
wherein the lower of said at least two electron treatment energies is between 3 MeV and 9 MeV and for operating the system at said lower electron treatment energy the at least one moderator is mounted in the path of the electron beam.

32. The system of claim 22, including a first and second energy moderator that may be selectively mounted in the path of the electron beam downstream from the linear accelerator,
wherein the system provides at least three clinically significantly different electron treatment energies between 3 MeV and 12 MeV,
wherein the linear accelerator operates at the same electron peak energy for all of said at least three electron treatment energies,
wherein the highest of said at least three electron treatment energies is between 9 MeV and 12 MeV and for operating the system at said highest electron treatment energy both said first and second moderator are removed from the path of the electron beam,
wherein the medium of said at least three electron treatment energies is between 6 MeV and 9 MeV and for operating the system at said medium electron treatment energy the first moderator is mounted in the path of the electron beam and the second moderator is removed from the path of the electron beam, and
wherein the lowest of said at least three electron treatment energies is between 3 MeV and 6 MeV and for operating the system at said lowest electron treatment energy either the second moderator is mounted in the path of the electron beam and the first moderator is removed from the path of the electron beam or the first and the second moderator are mounted in the path of the electron beam.

* * * * *